United States Patent
Nijmeijer et al.

(10) Patent No.: US 11,452,749 B2
(45) Date of Patent: Sep. 27, 2022

(54) MEANS AND METHODS FOR AAV GENE THERAPY IN HUMANS

(71) Applicant: uniQure IP B.V., Amsterdam (NL)

(72) Inventors: Bart Antonius Nijmeijer, Amsterdam (NL); Valerie Ferreira, Amsterdam (NL)

(73) Assignee: UNIQURE IP B.V., Amsterdam (NL)

( * ) Notice: Subject to any disclaimer, the term of this patent is extended or adjusted under 35 U.S.C. 154(b) by 1114 days.

(21) Appl. No.: 16/031,906

(22) Filed: Jul. 10, 2018

(65) Prior Publication Data

US 2019/0008909 A1 Jan. 10, 2019

(30) Foreign Application Priority Data

Jul. 10, 2017 (EP) ..................... 17180601

(51) Int. Cl.
*A61K 48/00* (2006.01)
*A61K 35/761* (2015.01)
*A61K 9/00* (2006.01)
*A61P 7/04* (2006.01)
*C12N 15/62* (2006.01)
*C12N 15/86* (2006.01)
*C07K 14/755* (2006.01)

(52) U.S. Cl.
CPC .......... *A61K 35/761* (2013.01); *A61K 9/0019* (2013.01); *A61K 48/0008* (2013.01); *A61K 48/0058* (2013.01); *A61K 48/0083* (2013.01); *A61P 7/04* (2018.01); *C12N 15/62* (2013.01); *C12N 15/86* (2013.01); *C07K 14/755* (2013.01); *C12N 2750/14143* (2013.01)

(58) Field of Classification Search
None
See application file for complete search history.

(56) References Cited

U.S. PATENT DOCUMENTS 10,512,675 B2 * 12/2019 Bunting ............. A61K 48/0008

OTHER PUBLICATIONS

BioMarin Pharmaceutical, "A Phase 1/2, Dose-Escalation Safety, Tolerability and Efficacy Study of BMN 270, an Adenovirus-Associated Virus Vector-Mediated Gene Transfer of Human Factor VIII in Patients With Severe Hemophilia A", ClinicalTrials,gov, Jun. 14, 2017, retrieved from the internet: URL:https://clinicaltrials.gov/ct2/show/record/NCT02576795. (6 pages).
Boutin et al., "Prevalence of Serum IgG and Neutralizing Factors Against Adeno-Associated Virus (AAV) Types 1, 2, 5, 6, 8, and 9 in the Healthy Population: Implications for Gene Therapy Using AAV Vectors", Human Gene Therapy, 2010, 21(6):704-712.
Dolgin, Elie, "Early clinical data raise the bar for hemophilia gene therapies", Nature Biotechnology, 2016, 34(10):999-1001.
European Extended Search Report for Application No. 17180601.1 dated Dec. 1, 2017. (9 pages).
Hildinger et al., "Hybrid Vectors Based on Adeno-Associated Virus Serotypes 2 and 5 for Muscle-Directed Gene Transfer", Journal of Virology, 2001, 75(3):6199-6203.
Leebeek et al., "Interim Results from a Dose Escalating Study of AMT-060 (AAV5-hFIX) Gene Transfer in Adult Patients with Severe Hemophilia B", Blood, 2016, 128:2314. (6 pages).
Mingozzi et al., "Immune responses to AAV vectors; overcoming barriers to successful gene therapy", Blood, 2013, 122(1):23-36.
Nathwani et al., "Safe and efficient transduction of the liver after peripheral vein infusion of self-complementary AAV vector results in stable therapeutic expression of human FIX in nonhuman primates", Blood, 2007, 109(4):1414-1421.
Sen et al., "Improved adeno-associated virus (AAV) serotype 1 and 5 vectors for gene therapy", Scientific Reports 3, Article No. 1832, 2013. (6 pages).
UniQuire Biopharma B.V., "Trial of AAV5-hFIX in Severe or Moderately Severe Hemophilia B", ClinicalTrials,gov, Feb. 3, 2017, retrieved from the internet: URL:https://clinicaltrials.gov/ct2/show/NCT02396342. (7 pages).

* cited by examiner

*Primary Examiner* — Celine X Qian
(74) *Attorney, Agent, or Firm* — Sunit Talapatra; Foley & Lardner LLP

(57) ABSTRACT

The present invention relates to means and method for AAV based gene therapies in humans. In particular, the present invention relates to the treatment of human patients that may be suspected to have antibodies directed against the AAV intended for use in the treatment.

10 Claims, 6 Drawing Sheets

Specification includes a Sequence Listing.

Figure 4 wtAAV5 - VP1 (SEQ ID NO.1)

MSFVDHPPDWLEEVGEGLREFLGLEAGPPKPKPNQQHQDQARGLVL
PGYNYLGPGNGLDRGEPVNRADEVAREHDISYNEQLEAGDNPYLKYN
HADAEFQEKLADDTSFGGNLGKAVFQAKKRVLEPFGLVEEGAKTAPT
GKRIDDHFPKRKKARTEEDSKPSTSSDAEAGPSGSQQLQIPAQPASSL
GADTMSAGGGGPLGDNNQGADGVGNASGDWHCDSTWMGDRVVTK
STRTWVLPSYNNHQYREIKSGSVDGSNANAYFGYSTPWGYFDFNRFH
SHWSPRDWQRLINNYWGFRPRSLRVKIFNIQVKEVTVQDSTTTIANNL
TSTVQVFTDDDYQLPYVVGNGTEGCLPAFPPQVFTLPQYGYATLNRD
NTENPTERSSFFCLEYFPSKMLRTGNNFEFTYNFEEVPFHSSFAPSQN
LFKLANPLVDQYLYRFVSTNNTGGVQFNKNLAGRYANTYKNWFPGPM
GRTQGWNLGSGVNRASVSAFATTNRMELEGASYQVPPQPNGMTNNL
QGSNTYALENTMIFNSQPANPGTTATYLEGNMLITSESETQPVNRVAY
NVGGQMATNNQSSTTAPATGTYNLQEIVPGSVWMERDVYLQGPIWA
KIPETGAHFHPSPAMGGFGLKHPPPMMLIKNTPVPGNITSFSDVPVSS
FITQYSTGQVTVEMEWELKKENSKRWNPEIQYTNNYNDPQFVDFAPD
STGEYRTTRPIGTRYLTRPL

Figure 5

AAV2 / AAV5 VP1 hybrid *(SEQ ID NO.2)

MAADGYLPDWLEDTLSEGIRQWWKLKPGPPPPKPAERHKDDSRGLV
LPGYKYLGPFNGLDKGEPVNEADAAALEHDKAYDRQLDSGDNPYLKY
NHADAEFQERLKEDTSFGGNLGRAVFQAKKRVLEPLGLVEEPVKTAPT
GKRIDDHFPKRKKARTEEDSKPSTSSDAEAGPSGSQQLQIPAQPASSL
GADTMSAGGGGPLGDNNQGADGVGNASGDWHCDSTWMGDRVVTK
STRTWVLPSYNNHQYREIKSGSVDGSNANAYFGYSTPWGYFDFNRFH
SHWSPRDWQRLINNYWGFRPRSLRVKIFNIQVKEVTVQDSTTTIANNL
TSTVQVFTDDDYQLPYVVGNGTEGCLPAFPPQVFTLPQYGYATLNRD
NTENPTERSSFFCLEYFPSKMLRTGNNFEFTYNFEEVPFHSSFAPSQN
LFKLANPLVDQYLYRFVSTNNTGGVQFNKNLAGRYANTYKNWFPGPM
GRTQGWNLGSGVNRASVSAFATTNRMELEGASYQVPPQPNGMTNNL
QGSNTYALENTMIFNSQPANPGTTATYLEGNMLITSESETQPVNRVAY
NVGGQMATNNQSSTTAPATGTYNLQEIVPGSVWMERDVYLQGPIWA
KIPETGAHFHPSPAMGGFGLKHPPPMMLIKNTPVPGNITSFSDVPVSS
FITQYSTGQVTVEMEWELKKENSKRWNPEIQYTNNYNDPQFVDFAPD
STGEYRTTRPIGTRYLTRPL

Figure 6

AAV5 - Ala insertion between AA1 and AA2 (SEQ ID NO.3)

MASFVDHPPDWLEEVGEGLREFLGLEAGPPKPKPNQQHQDQARGLV
LPGYNYLGPGNGLDRGEPVNRADEVAREHDISYNEQLEAGDNPYLKY
NHADAEFQEKLADDTSFGGNLGKAVFQAKKRVLEPFGLVEEGAKTAP
TGKRIDDHFPKRKKARTEEDSKPSTSSDAEAGPSGSQQLQIPAQPASS
LGADTMSAGGGGPLGDNNQGADGVGNASGDWHCDSTWMGDRVVT
KSTRTWVLPSYNNHQYREIKSGSVDGSNANAYFGYSTPWGYFDFNRF
HSHWSPRDWQRLINNYWGFRPRSLRVKIFNIQVKEVTVQDSTTTIANN
LTSTVQVFTDDDYQLPYVVGNGTEGCLPAFPPQVFTLPQYGYATLNR
DNTENPTERSSFFCLEYFPSKMLRTGNNFEFTYNFEEVPFHSSFAPSQ
NLFKLANPLVDQYLYRFVSTNNTGGVQFNKNLAGRYANTYKNWFPGP
MGRTQGWNLGSGVNRASVSAFATTNRMELEGASYQVPPQPNGMTN
NLQGSNTYALENTMIFNSQPANPGTTATYLEGNMLITSESETQPVNRV
AYNVGGQMATNNQSSTTAPATGTYNLQEIVPGSVWMERDVYLQGPI
WAKIPETGAHFHPSPAMGGFGLKHPPPMMLIKNTPVPGNITSFSDVPV
SSFITQYSTGQVTVEMEWELKKENSKRWNPEIQYTNNYNDPQFVDFA
PDSTGEYRTTRPIGTRYLTRPL

SEQUENCE LISTING

<160> NUMBER OF SEQ ID NOS: 3

<210> SEQ ID NO 1
<211> LENGTH: 724
<212> TYPE: PRT
<213> ORGANISM: adeno-associated virus 5

<400> SEQUENCE: 1

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
```

-continued

```
                225                 230                 235                 240

Ser Tyr Asn Asn His Gln Tyr Arg Glu Ile Lys Ser Gly Ser Val Asp
                        245                 250                 255

Gly Ser Asn Ala Asn Ala Tyr Phe Gly Tyr Ser Thr Pro Trp Gly Tyr
                        260                 265                 270

Phe Asp Phe Asn Arg Phe His Ser His Trp Ser Pro Arg Asp Trp Gln
                        275                 280                 285

Arg Leu Ile Asn Asn Tyr Trp Gly Phe Arg Pro Arg Ser Leu Arg Val
                        290                 295                 300

Lys Ile Phe Asn Ile Gln Val Lys Glu Val Thr Val Gln Asp Ser Thr
        305                 310                 315                 320

Thr Thr Ile Ala Asn Asn Leu Thr Ser Thr Val Gln Val Phe Thr Asp
                        325                 330                 335

Asp Asp Tyr Gln Leu Pro Tyr Val Val Gly Asn Gly Thr Glu Gly Cys
                        340                 345                 350

Leu Pro Ala Phe Pro Pro Gln Val Phe Thr Leu Pro Gln Tyr Gly Tyr
                        355                 360                 365

Ala Thr Leu Asn Arg Asp Asn Thr Glu Asn Pro Thr Glu Arg Ser Ser
                        370                 375                 380

Phe Phe Cys Leu Glu Tyr Phe Pro Ser Lys Met Leu Arg Thr Gly Asn
        385                 390                 395                 400

Asn Phe Glu Phe Thr Tyr Asn Phe Glu Glu Val Pro Phe His Ser Ser
                        405                 410                 415

Phe Ala Pro Ser Gln Asn Leu Phe Lys Leu Ala Asn Pro Leu Val Asp
                        420                 425                 430

Gln Tyr Leu Tyr Arg Phe Val Ser Thr Asn Asn Thr Gly Gly Val Gln
                        435                 440                 445

Phe Asn Lys Asn Leu Ala Gly Arg Tyr Ala Asn Thr Tyr Lys Asn Trp
                        450                 455                 460

Phe Pro Gly Pro Met Gly Arg Thr Gln Gly Trp Asn Leu Gly Ser Gly
        465                 470                 475                 480

Val Asn Arg Ala Ser Val Ser Ala Phe Ala Thr Thr Asn Arg Met Glu
                        485                 490                 495

Leu Glu Gly Ala Ser Tyr Gln Val Pro Pro Gln Pro Asn Gly Met Thr
                        500                 505                 510

Asn Asn Leu Gln Gly Ser Asn Thr Tyr Ala Leu Glu Asn Thr Met Ile
                        515                 520                 525

Phe Asn Ser Gln Pro Ala Asn Pro Gly Thr Thr Ala Thr Tyr Leu Glu
                        530                 535                 540

Gly Asn Met Leu Ile Thr Ser Glu Ser Glu Thr Gln Pro Val Asn Arg
        545                 550                 555                 560

Val Ala Tyr Asn Val Gly Gly Gln Met Ala Thr Asn Asn Gln Ser Ser
                        565                 570                 575

Thr Thr Ala Pro Ala Thr Gly Thr Tyr Asn Leu Gln Glu Ile Val Pro
                        580                 585                 590

Gly Ser Val Trp Met Glu Arg Asp Val Tyr Leu Gln Gly Pro Ile Trp
                        595                 600                 605

Ala Lys Ile Pro Glu Thr Gly Ala His Phe His Pro Ser Pro Ala Met
                        610                 615                 620

Gly Gly Phe Gly Leu Lys His Pro Pro Pro Met Met Leu Ile Lys Asn
        625                 630                 635                 640

Thr Pro Val Pro Gly Asn Ile Thr Ser Phe Ser Asp Val Pro Val Ser
                        645                 650                 655
```

```
Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
            675                 680                 685

Tyr Thr Asn Asn Tyr Asn Asp Pro Gln Phe Val Asp Phe Ala Pro Asp
            690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 2
<211> LENGTH: 725
<212> TYPE: PRT
<213> ORGANISM: Artificial Sequence
<220> FEATURE:
<223> OTHER INFORMATION: AAV2 / AAV5 VP1 hybrid

<400> SEQUENCE: 2

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Thr Gly Lys Arg
    130                 135                 140

Ile Asp Asp His Phe Pro Lys Arg Lys Lys Ala Arg Thr Glu Glu Asp
145                 150                 155                 160

Ser Lys Pro Ser Thr Ser Ser Asp Ala Glu Ala Gly Pro Ser Gly Ser
                165                 170                 175

Gln Gln Leu Gln Ile Pro Ala Gln Pro Ala Ser Ser Leu Gly Ala Asp
            180                 185                 190

Thr Met Ser Ala Gly Gly Gly Gly Pro Leu Gly Asp Asn Asn Gln Gly
            195                 200                 205

Ala Asp Gly Val Gly Asn Ala Ser Gly Asp Trp His Cys Asp Ser Thr
    210                 215                 220

Trp Met Gly Asp Arg Val Val Thr Lys Ser Thr Arg Thr Trp Val Leu
225                 230                 235                 240

Pro Ser Tyr Asn Asn His Gln Tyr Arg Glu Ile Lys Ser Gly Ser Val
                245                 250                 255

Asp Gly Ser Asn Ala Asn Ala Tyr Phe Gly Tyr Ser Thr Pro Trp Gly
            260                 265                 270

Tyr Phe Asp Phe Asn Arg Phe His Ser His Trp Ser Pro Arg Asp Trp
    275                 280                 285
```

-continued

```
Gln Arg Leu Ile Asn Asn Tyr Trp Gly Phe Arg Pro Arg Ser Leu Arg
    290                 295                 300
Val Lys Ile Phe Asn Ile Gln Val Lys Glu Val Thr Val Gln Asp Ser
305                 310                 315                 320
Thr Thr Thr Ile Ala Asn Asn Leu Thr Ser Thr Val Gln Val Phe Thr
                325                 330                 335
Asp Asp Asp Tyr Gln Leu Pro Tyr Val Val Gly Asn Gly Thr Glu Gly
                340                 345                 350
Cys Leu Pro Ala Phe Pro Pro Gln Val Phe Thr Leu Pro Gln Tyr Gly
            355                 360                 365
Tyr Ala Thr Leu Asn Arg Asp Asn Thr Glu Asn Pro Thr Glu Arg Ser
370                 375                 380
Ser Phe Phe Cys Leu Glu Tyr Phe Pro Ser Lys Met Leu Arg Thr Gly
385                 390                 395                 400
Asn Asn Phe Glu Phe Thr Tyr Asn Phe Glu Glu Val Pro Phe His Ser
                405                 410                 415
Ser Phe Ala Pro Ser Gln Asn Leu Phe Lys Leu Ala Asn Pro Leu Val
            420                 425                 430
Asp Gln Tyr Leu Tyr Arg Phe Val Ser Thr Asn Asn Thr Gly Gly Val
            435                 440                 445
Gln Phe Asn Lys Asn Leu Ala Gly Arg Tyr Ala Asn Thr Tyr Lys Asn
    450                 455                 460
Trp Phe Pro Gly Pro Met Gly Arg Thr Gln Gly Trp Asn Leu Gly Ser
465                 470                 475                 480
Gly Val Asn Arg Ala Ser Val Ser Ala Phe Ala Thr Thr Asn Arg Met
                485                 490                 495
Glu Leu Glu Gly Ala Ser Tyr Gln Val Pro Pro Gln Pro Asn Gly Met
                500                 505                 510
Thr Asn Asn Leu Gln Gly Ser Asn Thr Tyr Ala Leu Glu Asn Thr Met
            515                 520                 525
Ile Phe Asn Ser Gln Pro Ala Asn Pro Gly Thr Thr Ala Thr Tyr Leu
    530                 535                 540
Glu Gly Asn Met Leu Ile Thr Ser Glu Ser Glu Thr Gln Pro Val Asn
545                 550                 555                 560
Arg Val Ala Tyr Asn Val Gly Gly Gln Met Ala Thr Asn Asn Gln Ser
                565                 570                 575
Ser Thr Thr Ala Pro Ala Thr Gly Thr Tyr Asn Leu Gln Glu Ile Val
            580                 585                 590
Pro Gly Ser Val Trp Met Glu Arg Asp Val Tyr Leu Gln Gly Pro Ile
            595                 600                 605
Trp Ala Lys Ile Pro Glu Thr Gly Ala His Phe His Pro Ser Pro Ala
610                 615                 620
Met Gly Gly Phe Gly Leu Lys His Pro Pro Met Met Leu Ile Lys
625                 630                 635                 640
Asn Thr Pro Val Pro Gly Asn Ile Thr Ser Phe Ser Asp Val Pro Val
                645                 650                 655
Ser Ser Phe Ile Thr Gln Tyr Ser Thr Gly Gln Val Thr Val Glu Met
            660                 665                 670
Glu Trp Glu Leu Lys Lys Glu Asn Ser Lys Arg Trp Asn Pro Glu Ile
            675                 680                 685
Gln Tyr Thr Asn Asn Tyr Asn Asp Pro Gln Phe Val Asp Phe Ala Pro
    690                 695                 700
Asp Ser Thr Gly Glu Tyr Arg Thr Thr Arg Pro Ile Gly Thr Arg Tyr
```

Leu Thr Arg Pro Leu
            725

<210> SEQ ID NO 3
<211> LENGTH: 725
<212> TYPE: PRT
<213> ORGANISM: Artificial Sequence
<220> FEATURE:
<223> OTHER INFORMATION: AAV5 - insertion of ala between AA1 and AA2
<220> FEATURE:
<221> NAME/KEY: misc_feature
<222> LOCATION: (2)..(2)
<223> OTHER INFORMATION: ala insertion

<400> SEQUENCE: 3

Met Ala Ser Phe Val Asp His Pro Pro Asp Trp Leu Glu Val Gly
1               5                   10                  15

Glu Gly Leu Arg Glu Phe Leu Gly Leu Glu Ala Gly Pro Pro Lys Pro
            20                  25                  30

Lys Pro Asn Gln Gln His Gln Asp Gln Ala Arg Gly Leu Val Leu Pro
        35                  40                  45

Gly Tyr Asn Tyr Leu Gly Pro Gly Asn Gly Leu Asp Arg Gly Glu Pro
50                  55                  60

Val Asn Arg Ala Asp Glu Val Ala Arg Glu His Asp Ile Ser Tyr Asn
65                  70                  75                  80

Glu Gln Leu Glu Ala Gly Asp Asn Pro Tyr Leu Lys Tyr Asn His Ala
            85                  90                  95

Asp Ala Glu Phe Gln Glu Lys Leu Ala Asp Asp Thr Ser Phe Gly Gly
        100                 105                 110

Asn Leu Gly Lys Ala Val Phe Gln Ala Lys Lys Arg Val Leu Glu Pro
    115                 120                 125

Phe Gly Leu Val Glu Glu Gly Ala Lys Thr Ala Pro Thr Gly Lys Arg
130                 135                 140

Ile Asp Asp His Phe Pro Lys Arg Lys Lys Ala Arg Thr Glu Glu Asp
145                 150                 155                 160

Ser Lys Pro Ser Thr Ser Ser Asp Ala Glu Ala Gly Pro Ser Gly Ser
            165                 170                 175

Gln Gln Leu Gln Ile Pro Ala Gln Pro Ala Ser Ser Leu Gly Ala Asp
        180                 185                 190

Thr Met Ser Ala Gly Gly Gly Pro Leu Gly Asp Asn Asn Gln Gly
    195                 200                 205

Ala Asp Gly Val Gly Asn Ala Ser Gly Asp Trp His Cys Asp Ser Thr
210                 215                 220

Trp Met Gly Asp Arg Val Val Thr Lys Ser Thr Arg Thr Trp Val Leu
225                 230                 235                 240

Pro Ser Tyr Asn Asn His Gln Tyr Arg Glu Ile Lys Ser Gly Ser Val
            245                 250                 255

Asp Gly Ser Asn Ala Asn Ala Tyr Phe Gly Tyr Ser Thr Pro Trp Gly
        260                 265                 270

Tyr Phe Asp Phe Asn Arg Phe His Ser His Trp Ser Pro Arg Asp Trp
    275                 280                 285

Gln Arg Leu Ile Asn Asn Tyr Trp Gly Phe Arg Pro Arg Ser Leu Arg
290                 295                 300

Val Lys Ile Phe Asn Ile Gln Val Lys Glu Val Thr Val Gln Asp Ser
305                 310                 315                 320

```
Thr Thr Thr Ile Ala Asn Asn Leu Thr Ser Thr Val Gln Val Phe Thr
            325                 330                 335

Asp Asp Asp Tyr Gln Leu Pro Tyr Val Val Gly Asn Gly Thr Glu Gly
        340                 345                 350

Cys Leu Pro Ala Phe Pro Pro Gln Val Phe Thr Leu Pro Gln Tyr Gly
            355                 360                 365

Tyr Ala Thr Leu Asn Arg Asp Asn Thr Glu Asn Pro Thr Glu Arg Ser
        370                 375                 380

Ser Phe Phe Cys Leu Glu Tyr Phe Pro Ser Lys Met Leu Arg Thr Gly
385                 390                 395                 400

Asn Asn Phe Glu Phe Thr Tyr Asn Phe Glu Glu Val Pro Phe His Ser
            405                 410                 415

Ser Phe Ala Pro Ser Gln Asn Leu Phe Lys Leu Ala Asn Pro Leu Val
            420                 425                 430

Asp Gln Tyr Leu Tyr Arg Phe Val Ser Thr Asn Asn Thr Gly Gly Val
            435                 440                 445

Gln Phe Asn Lys Asn Leu Ala Gly Arg Tyr Ala Asn Thr Tyr Lys Asn
            450                 455                 460

Trp Phe Pro Gly Pro Met Gly Arg Thr Gln Gly Trp Asn Leu Gly Ser
465                 470                 475                 480

Gly Val Asn Arg Ala Ser Val Ser Ala Phe Ala Thr Thr Asn Arg Met
                485                 490                 495

Glu Leu Glu Gly Ala Ser Tyr Gln Val Pro Pro Gln Pro Asn Gly Met
            500                 505                 510

Thr Asn Asn Leu Gln Gly Ser Asn Thr Tyr Ala Leu Glu Asn Thr Met
            515                 520                 525

Ile Phe Asn Ser Gln Pro Ala Asn Pro Gly Thr Thr Ala Thr Tyr Leu
530                 535                 540

Glu Gly Asn Met Leu Ile Thr Ser Glu Ser Glu Thr Gln Pro Val Asn
545                 550                 555                 560

Arg Val Ala Tyr Asn Val Gly Gly Gln Met Ala Thr Asn Asn Gln Ser
                565                 570                 575

Ser Thr Thr Ala Pro Ala Thr Gly Thr Tyr Asn Leu Gln Glu Ile Val
            580                 585                 590

Pro Gly Ser Val Trp Met Glu Arg Asp Val Tyr Leu Gln Gly Pro Ile
            595                 600                 605

Trp Ala Lys Ile Pro Glu Thr Gly Ala His Phe His Pro Ser Pro Ala
610                 615                 620

Met Gly Gly Phe Gly Leu Lys His Pro Pro Met Met Leu Ile Lys
625                 630                 635                 640

Asn Thr Pro Val Pro Gly Asn Ile Thr Ser Phe Ser Asp Val Pro Val
            645                 650                 655

Ser Ser Phe Ile Thr Gln Tyr Ser Thr Gly Gln Val Thr Val Glu Met
            660                 665                 670

Glu Trp Glu Leu Lys Lys Glu Asn Ser Lys Arg Trp Asn Pro Glu Ile
            675                 680                 685

Gln Tyr Thr Asn Asn Tyr Asn Asp Pro Gln Phe Val Asp Phe Ala Pro
            690                 695                 700

Asp Ser Thr Gly Glu Tyr Arg Thr Thr Arg Pro Ile Gly Thr Arg Tyr
705                 710                 715                 720

Leu Thr Arg Pro Leu
            725
```

MEANS AND METHODS FOR AAV GENE THERAPY IN HUMANS

CROSS-REFERENCE TO RELATED APPLICATIONS

The present non-provisional U.S. Patent Application claims priority to European Patent Application No. 17180601.1, filed Jul. 10, 2017, the entire disclosure of which is incorporated herein by reference.

SEQUENCE LISTING

The instant application contains a Sequence Listing which has been submitted electronically in ASCII format and is hereby incorporated by reference in its entirety. Said ASCII copy, originally filed in European Patent Application No. 17180601.1, filed Jul. 10, 2017, is named 114188-1600_SL.txt and is 20,480 bytes in size.

FIELD OF THE INVENTION

The present invention relates to means and method for AAV based gene therapies in humans. In particular, the present invention relates to the treatment of human patients that may be suspected to have antibodies directed against the AAV intended for use in said treatment.

BACKGROUND OF THE INVENTION

Adeno-associated virus (AAV) is considered as one of the most promising viral vectors for human gene therapy. AAV has the ability to efficiently infect dividing as well as non-dividing human cells. The wild-type AAV viral genome integrates into a single chromosomal site in the host cell's genome, and most importantly, even though AAV is present in many humans it has not been associated with any disease. In view of these advantages, recombinant adeno-associated virus (rAAV) is being evaluated in gene therapy clinical trials for hemophilia B, malignant melanoma, cystic fibrosis, and other diseases. Numerous clinical trials and approval of gene therapy medicines in Europe, such as Alipogene tiparvovec (Glybera®, uniQure), holds a promise for AAV to become main stay of clinical practice.

One major challenge for a successful administration of AAV vector is to overcome the presence of neutralizing antibodies (immunoglobulins) (NAb) that have developed following exposure to wild-type AAV or AAV-based vectors. In both cases, the neutralizing serotype-specific antibodies directed towards the viral capsid proteins can reduce the efficiency of gene transfer with AAV of the same serotype.

Relatively lower endemic NAB titers were observed for the AAV5 serotype in humans as compared with other serotypes (Boutin et al. Hum Gene Ther 2010, 21:704-712). In the treatment of humans with AAV, already such low endemic NAB titers were reported to affect transduction and result in a severely reduced transgene expression (Manno et al., Nature Medicine, 2006, 12(3), 342-347). Hence, the general consensus in the field is to avoid treating patients having NAB titers altogether. Thus, the current practice in the clinic with regard to pre-existing immunity involves the screening of human patients for exclusion should patients have neutralizing antibodies against the AAV capsid (Brimble et al. Expert Opin Biol Ther 2016, 16(1):79-92 and Boutin et al. Hum Gene Ther 2010, 21:704-712). Immunosuppressive regimens have been tried in order to reduce the formation of NAb upon first administration to allow for a second administration (Corti et al., Mol Ther-Meth Clin Dev (2014) 1, 14033; Mingozzi et al. Mol Ther vol. 20 no. 7, 1410-1416; McIntosh et al. Gene Ther 2012, 19, 78-85)). Furthermore, strategies have been suggested to overcome pre-existing antibodies which include plasma exchange and the use of immunosuppressive regimens (e.g. Chicoine et al., Mol Ther 2014, vol. 22 no. 2 338-347; Hurlbut et al. Mol Ther 2010, vol. 18 no. 11 1983-1984 and Mingozzi et al. Mol Ther vol. 20 no. 7, 1410-1416). These strategies have been tested in animal models obtaining limited success.

Hence, there is a need in the art to enable the administration of rAAV gene therapy vectors in human patients that have, or may be suspected to have, AAV neutralizing antibodies.

BRIEF DESCRIPTION OF THE INVENTION

The current inventors have now surprisingly found that in particular for AAV5 gene therapy vectors, and in contrast to the suggestions in the state of the art, human patients that have endemic pre-existing anti-AAV5 antibodies (i.e. pre-existing anti-AAV5 antibodies resulting from endemic exposure) can be considered to be eligible for treatment. This is in contrast to the believe in the prior art that the presence of neutralizing antibodies should be considered as an exclusion criterion e.g. for patients participating in clinical trials. In other words, the believe in the state of the art is that patients that have antibodies against AAV5, more in particular endemic pre-existing antibodies against AAV5, are not considered eligible for treatment with an AAV5 gene therapy vector. The surprising finding disclosed herein that human patients that have endemic pre-existing anti-AAV5 antibodies can be considered to be eligible for treatment not only relates to a subpopulation of human patients that are e.g. found to have very low levels of pre-existing anti-AAV5 antibodies, but rather, it was found to relate essentially to most if not all patients of the human population that scores positive for pre-existing anti-AAV5 antibodies and that have not previously been subjected to any AAV5 gene therapy.

Hence, in one aspect, the current invention provides for an AAV5 gene therapy vector for use in a medical treatment of a human patient, wherein said human patient is not subjected to a pre-screening with an assay to determine anti-AAV5 antibodies and wherein said human has not been subjected to a medical treatment with an AAV5 gene therapy vector prior to said medical treatment. In other words, an AAV5 gene therapy vector is provided for use in a medical treatment of a human, wherein the anti-AAV5 antibody status is unknown and wherein said human has not been subjected to a medical treatment with an AAV5 gene therapy vector prior to said medical treatment. According to one aspect, the current invention may make it possible to treat patients, or to include patients in a clinical trial, that have not been treated with an AAV5 gene therapy vector before, without, prior to the medical treatment, screening for the presence of anti-AAV5 antibodies.

In a further aspect, an AAV5 gene therapy vector is provided for use in a medical treatment of a human, wherein said human is subjected to a pre-screening with an assay to determine anti-AAV5 antibodies and wherein said human has not been subjected to a medical treatment with an AAV5 gene therapy vector prior to said medical treatment, said human having an anti-AAV5 antibody level corresponding to at most the $100^{th}$ percentile, preferably at most the 95th percentile of anti-AAV5 antibody levels as observed in the human population. Preferably, said human patient tested positive for anti-AAV5 antibodies.

DESCRIPTION OF THE FIGURES

FIG. 1A: Neutralization results of the ten pre-dosing samples. Fifty-percent mark is shown as a dotted line. FIG. 1B: Curve fitting results of three positive samples 3, 4, 5. A four-parameter curve was fitted by means of non-linear regression. Titers were calculated as the theoretical dilution at which the fitted curve passed the 50% mark (shown above horizontal axis).

FIG. 4. Depicted is the VP1 amino acid sequence of a wild-type AAV5. The amino acid start positions of VP2 (T, due to ACG initiation site) and VP3 (M), are underlined.

FIG. 5. Depicted is the VP1 amino acid sequence of a hybrid VP1 sequence, consisting of an N-terminus AAV2 derived VP1 sequence (underlined) linked with AAV5 derived VP2 and VP3 encoding sequence. The VP1 protein is thus a hybrid AAV2/AAV5 capsid protein. Expression constructs used for AAV capsids that encode said hybrid VP1, can encode VP2 and VP3 sequences as well, which will not be hybrid VP2 and VP3 capsid proteins, but wild-type sequence AAV5 VP2 and VP3 proteins.

FIG. 6. Shown is the VP1 amino acid sequence of a wild-type AAV5, having an insertion of an Ala in between positions 1 and 2 of the wild-type AAV5 sequence. Hence, the VP1 capsid consists of an AAV5 wild-type sequence with an inserted amino acid, and VP2 and VP3 proteins encoded are wild-type AAV5 VP2 and VP3 proteins without modifications.

DEFINITIONS

Figure 1A:
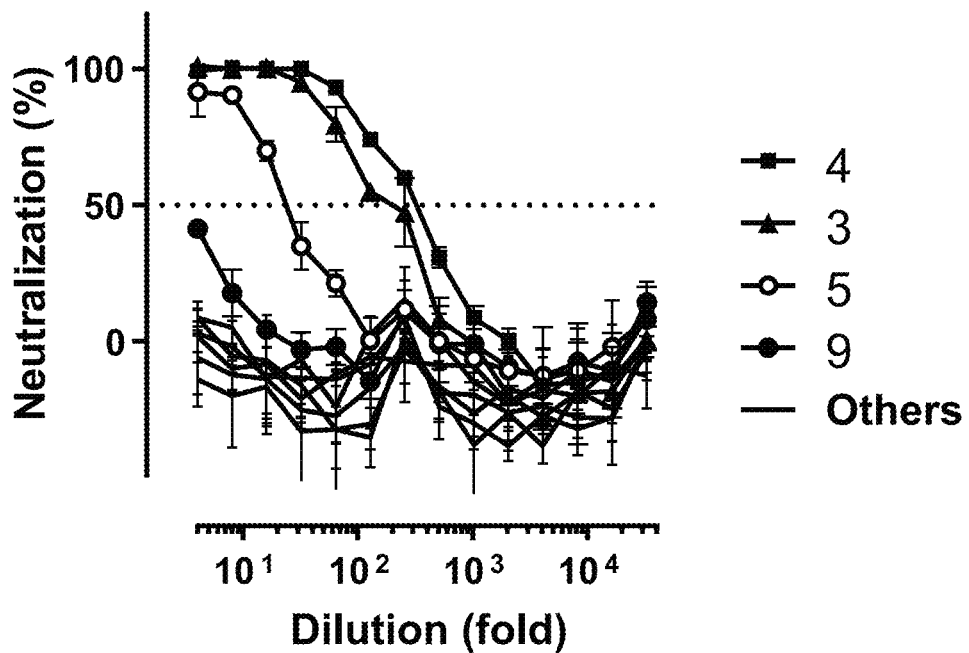
FIGS. 1A and 1B: NAb assay results of pre-treatment samples.

An "AAV vector" refers to a recombinant adeno-associated virus (AAV) vector which is derived from the wild type AAV by using molecular methods. An AAV vector is distinguished from a wild type (wt) AAV vector, since at least a part of the viral genome has been replaced with a transgene, which is a non-native nucleic acid with respect to the wild-type AAV nucleic acid sequence.

The AAV vector, including combinations of AAV capsid and AAV genome ITRs, can be produced using methods known in the art, as described in Pan et al. (J. of Virology (1999) 73: 3410-3417), Clark et al. (Human Gene Therapy (1999) 10: 1031-1039), Wang et al. (Methods Mol. Biol. (2011) 807: 361-404) and Grimm (Methods (2002) 28(2): 146-157), which are incorporated herein by reference. Alternatively, AAV vectors can be produced in insect cells using a baculovirus expression system (BEVS). The initial baculovirus system for production of rAAV was described by Urabe et al (Urabe et al. [2002] Human Gene Therapy 13(16):1935-1943) and consists of three baculoviruses, namely Bac-Rep, Bac-cap and Bac-vec, co-infection of which into insect cells e.g. SF9 resulted in generation of rAAV. The properties of such produced rAAV, i.e. physical and molecular characteristic including potency, did not differ significantly from the rAAV generated in mammalian cells (Urabe [2002] supra). The initial baculovirus system by Urabe (2002, supra) has been further developed (see e.g., Kohlbrenner et al. (2005) Molecular Therapy 12 (6):1217-1225; Urabe et al. (2006) Journal of Virology 80(4):1874-1885; WO 2007/046703; WO 2007/148971; WO 2009/014445 and WO 2009/104964).

The term "transgene" is used to refer to a non-native nucleic acid with respect to the AAV nucleic acid sequence. It is used to refer to a polynucleotide that can be introduced into a cell or organism. Transgenes include any polynucleotide, such as a gene that encodes a polypeptide or protein, a polynucleotide that is transcribed into an inhibitory polynucleotide, or a polynucleotide that is not transcribed (e.g., lacks an expression control element, such as a promoter that drives transcription). A transgene is preferably inserted between inverted terminal repeat (ITR) sequences. A transgene may also be an expression construct comprising an expression regulatory element such as a promoter or transcription regulatory sequence operably linked to a coding sequence and a 3' termination sequence.

"Transduction" refers to the transfer of a transgene into a recipient host cell by a viral vector. Transduction of a target cell by an rAAV vector of the invention leads to transfer of the transgene contained in that vector into the transduced cell. "Host cell" or "target cell" refers to the cell into which the DNA delivery takes place, such as, for example, the synoviocytes or synovial cells of an individual. AAV vectors are able to transduce both dividing and non-dividing cells.

"Gene" or "coding sequence" refers to a DNA or RNA region which "encodes" a particular protein. A coding sequence is transcribed (DNA) and translated (RNA) into a polypeptide when placed under the control of an appropriate regulatory region, such as a promoter. A gene may comprise several operably linked fragments, such as a promoter, a 5' leader sequence, an intron, a coding sequence and a 3' nontranslated sequence, comprising a polyadenylation site or a signal sequence. A chimeric or recombinant gene is a gene not normally found in nature, such as a gene in which for example the promoter is not associated in nature with part or all of the transcribed DNA region. "Expression of a gene" refers to the process wherein a gene is transcribed into an RNA and/or translated into an active protein.

"Sequence identity" and "sequence similarity" can be determined by alignment of two peptides or two nucleotide sequences using global or local alignment algorithms, depending on the length of the two sequences. Sequences of similar lengths are preferably aligned using a global alignment algorithm (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have substantially different overall lengths, local alignments, such as those using the Smith Waterman algorithm, are preferred. Alternatively, percentage similarity or identity may be determined by searching against public databases, using algorithms such as FASTA, BLAST, etc.

As used herein, "gene therapy" is the insertion of nucleic acid sequences (e.g., a transgene as defined herein) into an individual's cells and/or tissues to treat a disease. The transgene can be a functional mutant allele that replaces or supplements a defective one. Gene therapy also includes insertion of transgene that are inhibitory in nature, i.e., that inhibit, decrease or reduce expression, activity or function of an endogenous gene or protein, such as an undesirable or aberrant (e.g., pathogenic) gene or protein. Such transgenes may be exogenous. An exogenous molecule or sequence is understood to be molecule or sequence not normally occurring in the cell, tissue and/or individual to be treated. Both acquired and congenital diseases are amenable to gene therapy. An AAV5 gene therapy vector thus refers to an AAV5 vector for use in gene therapy.

In this document and in its claims, the verb "to comprise" and its conjugations is used in its non-limiting sense to mean that items following the word are included, but items not specifically mentioned are not excluded.

In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "approximately" or "about" when used in association with a numerical value (approximately 10, about 10) preferably means that the value may be the given value of 10 more or less 10% of the value.

DETAILED DESCRIPTION OF THE INVENTION

As said, surprisingly it was found that in particular for AAV5 gene therapy vectors, human patients that have endemic pre-existing anti-AAV5 antibodies can be considered to be eligible for treatment. This is in contrast to the general belief that the presence of pre-existing anti-AAV antibodies against a particular serotype is to preclude gene therapy treatment with said serotype. Without being bound by theory, AAV5 may be a serotype for which the endemic pre-existing anti-AAV5 antibody titers as they are found in the human population is relatively low as compared with other serotypes. This may be because of the route of infection, which may be different between serotypes, and/or may be with or without co-infection of a helper virus. Furthermore, AAV5 is most divergent from other primate AAV serotypes and phylogenetically separate therefrom, which may also contribute thereto. Regardless of what lies at the root of the current invention, it allows for most if not all of the human population to be eligible for treatment with AAV5 serotype based gene therapies or the like. This includes the subset of the human population that is negative with regard to anti-AAV5 antibodies, and also the subset of the human population that was found positive with regard to anti-AAV5 antibodies, not including the (currently) very minor subset of the human population that has been subjected to an AAV5 gene therapy treatment or the like. In the human population that has been subjected to an AAV5 gene therapy treatment such high titers of anti-AAV5 antibodies are observed (about $10^4$ or more as compared with endemically AAV5 infected humans) that these are believed to be non-eligible for treatment with AAV5 gene therapy vectors or the like.

Hence, in a first aspect of the invention, an AAV5 gene therapy vector is provided for use in a medical treatment of a human, wherein said human is not subjected to a pre-screening with an assay to determine anti-AAV5 antibodies and wherein said human has not been subjected to a medical treatment with an AAV5 gene therapy vector prior to said medical treatment.

The complete genome of AAV5 and other AAV serotypes has been sequenced (Chiorini et al. 1999, J. of Virology Vol. 73, No. 2, p 1309-1319) and the nucleotide sequence is available in GenBank (Accession No. AF085716; 23 Feb. 2015). It is understood that wild-type AAV5 based gene therapy vectors comprise at least AAV5 capsid proteins comprising VP1, VP2 and VP3 capsid proteins corresponding to said amino acid sequence sequences or at least substantially identical. Substantially identical therewith including having at least 80%, at least 85%, at least 90% or at least 95% amino acid sequence identity therewith. An AAV5 capsid VP1 protein sequence against which sequence identity can be determined is shown in FIG. 4. Such sequences can be naturally occurring sequences of AAV viruses that fall from a phylogenetic perspective in the AAV5 clade (e.g. as depicted in FIG. 4).

A "serotype" is traditionally defined on the basis of a lack of cross-reactivity between antibodies to one virus as compared to another virus. Such cross-reactivity differences are usually due to differences in capsid protein sequences/antigenic determinants (e.g., due to VP1, VP2, and/or VP3 sequence differences of AAV serotypes). Under the traditional definition, a serotype means that the virus of interest has been tested against serum specific for all existing and characterized serotypes for neutralizing activity and no antibodies have been found that neutralize the virus of interest. As more naturally occurring virus isolates are discovered and capsid mutants generated, there may or may not be serological differences with any of the currently existing serotypes. For the sake of convenience, AAV5 serotypes include AAV with capsid sequence modifications that have not been characterized as being a distinct serotype, which may also constitute a subgroup or variant of the AAV5 serotype. Such variants in general having substantial sequence identity.

Non-natural capsid sequences may also be contemplated in accordance with the invention, e.g. amino acid sequences exposed to the serum (exposed to the outside world) may be derived from one serotype, whereas non-exposed amino acid sequences within a capsid may be from other serotypes and/or allow for more variation. As the crystal structure of AAV5 (e.g. Govindasamy et al. J. Virol. October 2013, vol. 87 no. 20; 11187-11199) is known, sequences that are not exposed and e.g. at the interior of the AAV5 capsid may be exchanged for sequences from other serotypes and/or allow for more sequence variation. For example, the VP1 amino acid sequence not contained in VP2 and VP3 is positioned at the interior. This sequence may e.g. be from serotype 2, whereas the VP2 and VP3 amino acid sequences may be entirely based on AAV5 (see e.g. FIG. 5). Such an AAV5 gene therapy vector capsid being from a serotype perspective and neutralizing antibody perspective indistinguishable from a fully wild-type capsid (see i.a. WO2000028004 and Urabe et al. J Virol, February 2006, Vol. 80, No. 4 p. 1874-1885). Such non-natural capsid sequences are hybrid sequences, and such hybrid vectors are also understood to be AAV5 gene therapy vectors in accordance with the invention. Furthermore, AAV5 capsid sequences may also have one or more amino acids inserted or replaced to enhance manufacturing and/or potency of a vector, such as i.a. described in WO2015137802, and as shown e.g. in FIG. 6. Such minor modified AAV5 capsids may also be regarded to be of the AAV5 serotype.

It is understood that the AAV5 vectors, or AAV5 gene therapy vectors, according to the invention relate to an AAV5 vector capsid, that encompasses a vector genome having a gene of interest comprised in between AAV inverted repeats, which may be AAV5 ITRs but not necessarily so. Hence, the AAV5 vectors according to the invention are delivery vehicles that are to deliver their payload, a vector genome having a transgene, e.g. a transgene that is to be of benefit to the human, to their target cells, e.g. liver cells, or heart muscle cells. Hence, AAV5 vectors can be considered to be of use in a medical treatment of a human, e.g. a human patient suffering from a disease which may be ameliorated due to the delivery of the transgene. As shown in the examples, the transgene can be FIX, or variants, such as the Padua mutant, thereof, but the transgene is not limiting in any way and further transgenes may be contemplated in the invention as described herein. Also, in one further embodiment, the human patient may be a male human patient.

In another embodiment, an AAV5 gene therapy vector is provided for use in a medical treatment of a human, wherein the anti-AAV5 antibody status is unknown (e.g. has not been determined) and wherein said human has not been subjected to a medical treatment with an AAV5 gene therapy vector prior to said medical treatment. As said, it may be not needed to test for the existence of antibodies against AAV5 in such patient. As shown in the example section, about 30% of the human population is shown to be positive with regard to the presence of TAb or NAb in the serum. Because it may not be needed to test for TAb or NAb in the serum, the population size that is eligible for treatment increases considerably, moreover it makes the treatment and selection of eligible patients more convenient as there is no need to perform a NAb or TAb assay before treatment can commence. All that may be needed is to know whether or not the human patient has been subjected to AAV5 gene therapy treatment before. It may be contemplated, that the prior treatment with an AAV gene therapy treatment may not be restricted solely to AAV5 but may include treatment with other serotypes as well, e.g. serotype 8. For such subjects it may be contemplated to do include a NAb or TAb assay or test as described in the example section in order to confirm that the NAb or TAb titer in the serum remains within the range as observed in naïve untreated human patients.

In another embodiment, an AAV5 gene therapy vector is provided for use in a medical treatment of a human, wherein said human is subjected to a pre-screening with an assay to determine anti-AAV5 antibodies and wherein said human has not been subjected to a medical treatment with an AAV5 gene therapy vector prior to said medical treatment, said human having an anti-AAV5 antibody level corresponding to at most the 95th percentile of anti-AAV5 antibody levels as observed in the human population. In this embodiment, a human patient which may benefit from a gene therapy treatment, is pre-screened with an anti-AAV5 antibody assay. As shown in the example section, the range of levels of anti-AAV5 antibodies observed in the human population, i.e. the range of anti-AAV5 antibody levels observed is from about 0, or about 1, to about 10,000.

Figure 3:
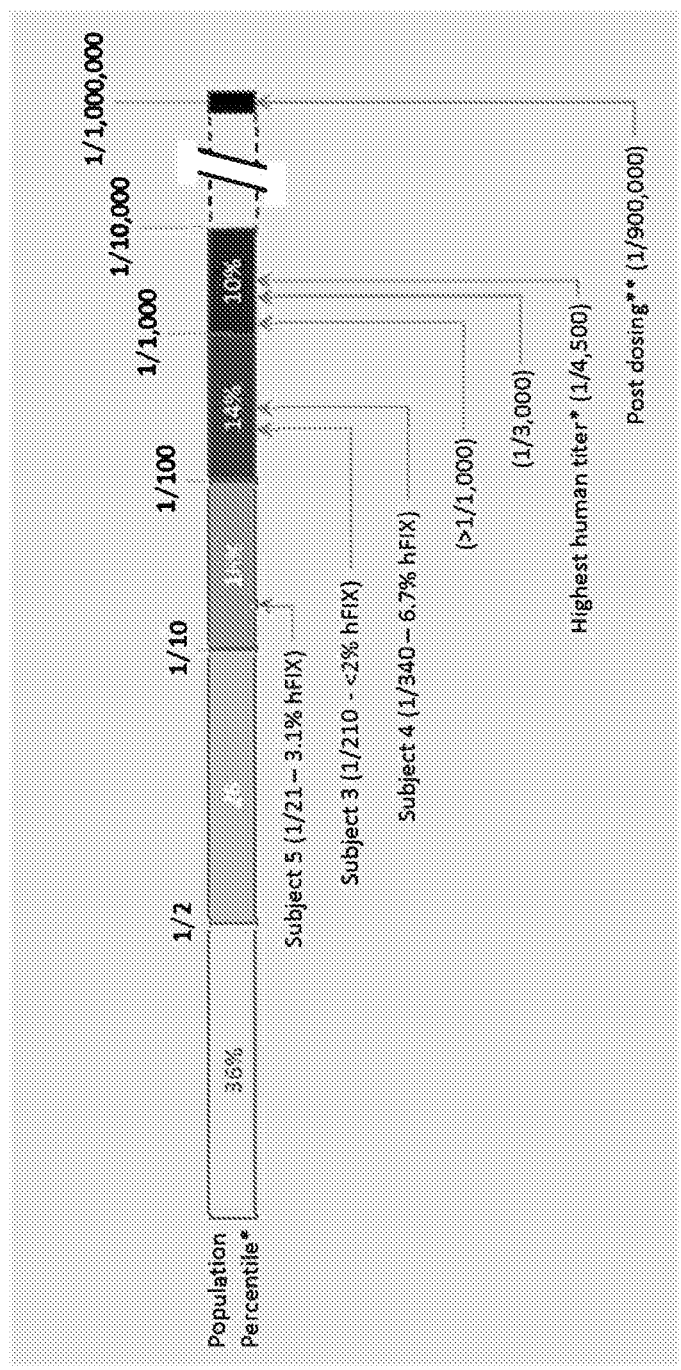
FIG. 3: AAV NAb titer scale. The percentiles of the human population (50 subjects) is depicted for NAb titers against AAV5. Note that the NAb titers observed in the human population are well outside of the NAb titers observed in AAV5 treated human patients.

The $n^{th}$ Percentile herein is typically defined as the proportion of the human population, n %, that is within in a distribution from 0% to n % that have an anti-AAV5 antibody level as determined with a NAb assay or TAb assay such as for instance described in the examples. For instance, when a human patient in a population (not before treated with an AAV5 vector) has an anti-AAV5 antibody level as determined with a NAb assay as described in the examples, the anti-AAV5 antibody level detected in the entire population is to be at most 10,000, as it is estimated that up to about 100% of the human population will be included. It may be preferred to treat a human patient when having an anti-AAV5 antibody level up to the $95^{th}$ percentile, which corresponds to a NAb level as determined with an assay as described in the examples of at most 4,500. It may be preferred to treat a human patient when having an anti-AAV5 antibody level up to the $93^{rd}$ percentile or $90^{th}$ percentile which corresponds to a NAb level as determined with an assay as described in the examples of at most 3,000 or 1,000, respectively (see FIG. 3). According to another embodiment, it may be preferred to treat a human patient when having an anti-AAV5 antibody level up to the $99^{th}$, $98^{th}$, $97^{th}$, $96^{th}$, $95^{th}$, $94^{th}$, $93^{rd}$, $92^{nd}$, $91^{st}$, $90^{th}$, $80^{th}$, or $70^{th}$ percentile. Nevertheless, it may be anticipated that most of the population, if not all, is eligible for treatment regardless of the anti-AAV5 antibody titer. As shown in the example section, any anti-AAV5 antibody assay suffices, i.e. either a NAb assay or a TAb assay or the like may be utilized to determine the antibody titers of the human population in order to determine the $95^{th}$ percentile, the $93^{rd}$ percentile or $90^{th}$ percentile. The selected human population remains the same while the actual values in titers may vary (up to 10,000 for the NAb assay of the examples or up to 5 for the TAb assay). This is because the values of titers observed are merely a number which only have relevance when put into perspective of titers in a population. It is understood that in any case the anti-AAV5 antibody titer levels as determined in the population relates to a human population of at least 50 humans as described in the example section.

Hence, in a further embodiment, an AAV5 gene therapy vector is provided for use in a medical treatment of a human, wherein said human is subjected to a pre-screening with an assay to determine anti-AAV5 antibodies and wherein said human has not been subjected to a medical treatment with an AAV5 gene therapy vector prior to said medical treatment, said human having an anti-AAV5 antibody level as determined in a NAb ELISA assay as described in the examples corresponding to at most the 95th percentile of anti-AAV5 antibody levels as observed in the human population. According to another embodiment, it may be preferred to treat a human patient when having an anti-AAV5 antibody level up to the $99^{th}$, $98^{th}$, $97^{th}$, $96^{th}$, $95^{th}$, $94^{th}$, $93^{rd}$ $92^{nd}$, $91^{st}$, $90^{th}$, $80^{th}$, or $70^{th}$ percentile.

It is understood that in accordance with the invention, now the subpopulation of the human population that previously would not have been considered eligible for treatment with AAV5 would now be considered eligible for treatment with an AAV5 gene therapy vector, in spite of testing positive in an anti-AAV5 antibody assay. Hence, in a further embodiment, an AAV5 gene therapy vector is provided for use in a medical treatment of a human, wherein said human tested positive for anti-AAV5 bodies, and wherein said human has not been treated previously with AAV5 or the like.

In a different embodiment, as in the current embodiment it is shown that the AAV5 antibody levels in the endemic, untreated human population allow for an efficient AAV5 gene therapy treatment, the current inventions also may allow for the treatment of human patients that have been subjected with an AAV gene therapy treatment, i.e. AAV5. For example, means and methods are known in the art that can reduce the levels of antibodies in the blood and thereby reducing the levels of ant-AAV5 antibodies as well. Such extracorporeal treatments of the blood wherein antibodies are removed from the blood can be employed to reduce the anti-AAV5 antibody titers in the blood to achieve the same levels as observed from endemic exposure, i.e. in endemic, untreated human population. Such methods are known in the art and can include e.g. plasmapheresis (Chicoine et al., Mol Ther 2014, vol. 22 no. 2 338-347). Hence, any method that can be employed to lower antibodies in the blood, including anti-AAV5 antibodies, may be utilized in the invention to reduce the anti-AAV5 antibody titer to such an extent that human patients, that previously were not eligible for treatment because they were previously subjected to an AAV5 based gene therapy treatment, obtain anti-AAV5 antibody titers as observed in the endemic human population and can be subjected to an AAV5 based gene therapy.

In another aspect of the invention, said AAV5 gene therapy vector as described above is administered at a dosage corresponding with at least $10^{11}$ capsids/kg of body weight. It is understood that the observation that we made with regard to the presence of anti-AAV5 antibodies may be dose dependent. In other words, at the dosages used, the concentration and/or amount of anti-AAV5 antibodies does not impair transduction. The amount of AAV5 gene therapy vector administered to a human patient in a treatment in order to obtain e.g. a meaningful level of transgene expression is far in excess of the anti-AAV5 antibodies present in the blood. From this perspective there may not be considered an upper limit. Nevertheless, an upper limit that may be considered is at a dosage corresponding with at most $10^{16}$ capsids/kg of body weight. It is understood that dosages may be set at dosage per patient or dosage per blood volume. A dosage of at least $10^{12}$ capsid/kg of body translates to about $10^{14}$ capsids per patient or about $10^{13}$ capsids/L blood volume of a patient, based on an average body weight of about 85 kg and average blood volume of 5 L. Hence, whatever dose range contemplated, these may easily be recalculated based on these parameters. Preferably the dosage corresponds to at least $1\times10^{12}$ capsids/kg of body weight, at least $5\times10^{12}$ capsids/kg of body weight, or at least $1\times10^{13}$ capsids/kg of body weight. The dosage used in the example section is of about $5\times10^{13}$ capsids/kg of body weight and about $2\times10^{14}$ capsids/kg of body weight. AAV Quantification of AAV capsid particle titers is easily determined and is well known in the art (i.a. Kohlbrenner et al., Hum Gene Ther Meth. June 2012, Vol. 23, No. 3: 198-203; Grimm et al., Gene Ther., Vol. 6, Nr. 7, p, 1322-1330, 1999).

The dosage selected may also be based on genomic copies. Genomic copies meaning the amount of vector genomes contained in the AAV5 preparation. The gc titer of an AAV5 vector preparation can easily be determined by using a qPCR that quantifies a vector genomic sequence. Preferably said AAV5 gene therapy vector is used at a dosage corresponding with at least $5\times10^{11}$ gc/kg of body weight. A dosage of at least $5\times10^{11}$ capsid/kg of body translates to about $5\times10^{12}$ gc per patient or about $10^{12}$ gc/L blood volume of a patient, based on an average body weight of about 85 kg and average blood volume of 5 L. Hence, whatever dose range contemplated, these may easily be recalculated based on these parameters. The dosage selected may be at least $1\times10^{12}$ gc/kg of body weight, at least $2\times10^{12}$ gc/kg of body weight, or $4\times10^{12}$ gc/kg of body weight. The dosage used in the example section being of about $5\times10^{12}$ gc/kg of body weight and about $2\times10^{13}$ gc/kg of body weight. Although there may not be an upper limit, this may be set to correspond to a dosage corresponding with at most $10^{15}$ gc/kg of body weight.

As said, the AAV5 gene therapy vector in accordance with the invention is for use in a medical treatment. The transgene contained within the AAV viral vector in accordance with the invention may not be a limitation of this invention. Nevertheless, preferably, and in accordance with the examples, the therapeutic gene encodes for human factor IX, as described in Nathwani et al. N Engl J Med 2011; 365(25): 2357-65 and Nathwani et al. B. N Engl J Med 2014; 371(21): 1994-200, and may including variants thereof such as described in WO2010029178, WO1999003496, WO2015086406 and WO2010012451, which are incorporated herein by reference in its entirety. In particular, it has been shown in the example section that therapeutically meaningful amounts of protein can be obtained with FIX encoding AAV5 vectors in human patients. Such may be useful e.g. in the treatment of hemophilia A or hemophilia B.

Hence, accordingly, an AAV5 gene therapy vector for use in a medical treatment of a human according to the invention, said AAV5 gene therapy vector is used in the treatment of Hemophilia B, the amount of transgenic FIX protein obtained in the plasma can be in the range between about 0.02 microgram/ml up to about 5 ug/ml. Alternatively, said AAV5 gene therapy vector when used in the treatment of hemophilia B patients having a severe phenotype obtain after treatment a moderate or mild phenotype or even a phenotype as observed in healthy individuals. Hemophilia B can be classified into three classes, each of which is characterized by the presence of different plasma concentrations of FIX. In severe hemophilia B the plasma levels of FIX activity are below 1% of normal; in the moderate form, levels are between 1% and 5%; in the mild form, between 5 and 25% of normal levels. There are healthy carrier individuals who have medium FIX activity levels, between 25% and 50% of normal, but many carriers can have levels even exceeding 50%.

Likewise, it can be expected that therapeutically effective amounts of other genes of interest are well within the reach of the skilled person. Hence, the invention is anticipated to be useful with any transgene. Further suitable transgenes for delivery to a patient in a viral vector for gene therapy may be selected by those of skill in the art. These therapeutic nucleic acid sequences typically encode products (e.g. proteins or RNA) for administration and expression in a patient in vivo or ex vivo to treat an inherited or non-inherited genetic defect, e.g. by replacing or correcting deficiency, to treat an epigenetic disorder or disease, or to treat a condition associated with dysregulation of a gene product. Such therapeutic genes which are desirable for the performance of gene therapy include, without limitation, a very low density lipoprotein receptor gene (VLDL-R) for the treatment of familial hypercholesterolemia or familial combined hyperlipidemia, the cystic fibrosis transmembrane regulator gene (CFTR) for treatment of cystic fibrosis, DMD Becker allele for treatment of Duchenne muscular dystrophy, and a number of other genes which may be readily selected by one of skill in the art to treat a particular disorder or disease. In a preferred embodiment, the rAAV vector comprises a transgene which encodes a therapeutic protein, or an RNA, such as a miRNA. Preferably, the therapeutic protein is selected from the group consisting of factor IX (preferably human factor IX), factor VIII (preferably human factor VIII), lipoprotein lipase (LPL; including mutants such as for example $LPL^{S447X}$; see WO 01/00220 A2), porphobilinogen deaminase (PBGD), very low density lipoprotein receptor (VLDL-R), cystic fibrosis transmembrane conductance regulator (CFTR), Duchenne muscular dystrophy (DMD) Becker allele, hypoxyluria (AGXT), N-acetyl-alpha-D-glucosaminidase (NaGlu), glial cell line-derived neurotrophic factor (GDNF), S100A1 (also known as S100 calcium-binding protein A1, which in humans is encoded by the S100A1 gene). In a preferred embodiment, the therapeutic protein is factor IX, more preferably human factor IX.

Alternatively, or in combination with any one of the preceding embodiments, in a preferred embodiment, the gene therapy is for treating, preventing, curing and/or reverting a condition or disease, preferably a so-called orphan disease, which is herein understood to be a rare disease that affects a small percentage of the population, e.g. fewer than 1 in 1,500 people of the population that is life-threatening, chronically debilitating and/or inadequately treated. Generally, an orphan disease is a genetic disease and hence a life-long disease even if symptoms do not immediately appear. In a preferred embodiment such condition or disease is selected from the group consisting of lipoprotein lipase deficiency (LPLD), hemophilia B, acute intermittent porphyria (AIP), Sanfilippo B syndrome, Parkinson's Disease (PD), congestive heart failure (CHF), Hemophilia A, Huntington's disease, Duchenne Muscular Dystrophy (DMD), Leber's congenital amaurosis, X-linked severe combined immunodeficiency (SCID), adenosine deaminase deficiency severe combined immunodeficiency (ADA-SCID), adrenoleukodystrophy, chronic lymphocytic leukemia, acute lymphocytic leukemia, multiple myeloma, cystic fibrosis, sickle cell disease, hyperlipoproteinemia type I, thalassemia, Alzheimer's disease, amyotrophic lateral sclerosis (ALS), epilepsy, Friedreich's ataxia, Fanconi anemia, Batten disease, wet AMD, alfa-antitrypsin-1, Pompe disease, SMA-1, Drug-resistant non-small cell lung cancer, GM1 gangliosidosis, retina pigmentosa, homozygous Familial Hypercholesterolemia, lysosomal storage diseases, a copper or iron accumulation disorders (e.g., Wilson's or Menkes disease), lysosomal acid lipase deficiency, hypoxyluria, Gaucher's disease, Hurler's disease, adenosine deaminase deficiency, glycogen storage disease and a retinal degenerative disease (such as RPE65 deficiency, choroideremia).

In a further embodiment, said AAV5 gene therapy vector is for use in a medical treatment of a human in accordance with the invention, wherein said use comprises administration into the bloodstream, e.g. administration of the AAV5 gene therapy vector to the bloodstream. The blood can contain anti-AAV5 antibodies, and in particular a delivery route via the bloodstream, e.g. via an intravascular infusion or injection, is contemplated. Delivery via the bloodstream allows for delivery of the AAV5 vector to the target tissue. Such delivery to the target tissue may occur by systemic delivery. The current invention is not limited to administration into the bloodstream. Indeed, conventional and pharmaceutically acceptable routes of administration that may be contemplated include direct delivery to the target organ, tissue or site (e.g. liver or the CNS), intranasal, intravenous, intramuscular, subcutaneous, intradermal, oral and other parental routes of administration. A preferred target tissue that may be contemplated is however the liver. Hence, most preferred, the AAV5 gene therapy vector delivers its transgene to the liver via an administration route via the bloodstream. As said, the AAV5 viral vector is administered in sufficient amounts to transfect the desired cells and provide sufficient levels of transduction and expression of the selected transgene to provide a therapeutic benefit without undue adverse or with medically acceptable physiological effects which can be determined by those skilled in the medical arts. Routes of administration may also be combined, if desired. Dosages of the rAAV vector (i.e. the AAV5 gene therapy vector) will depend primarily on factors such as the condition being treated, the selected gene, the age, weight and health of the patient, and may thus vary among patients.

The AAV5 gene therapy vector for use in a medical treatment of a human in accordance with the invention, is preferably an AAV5 gene therapy vector produced in insect cells. Without being bound by theory, the method of production may play a role in the immunity profile associated with an AAV vector, as AAV capsids may differ when produced in insect cells from AAV capsids produced in mammalian cells. This difference may be with regard to glycosylation or other post-translational modification. Furthermore, mammalian cell based manufacturing may have the downside that rep and cap expression constructs be contained within AAV capsids that are administered to the patients, resulting in transfer of rep and cap expression constructs, albeit at very low amounts, to the human subjects. Expression of AAV rep and cap in a human patient may be detrimental from an immunity perspective, in particular in case of human patients that would test positive with regard to anti-AAV5 antibodies. Hence, it may be preferred that the AAV5 viral vector that is to be administered to human patients is produced in insect cells. Insect cell based manufacturing is well established and includes, but is not limited to, means and methods as described in WO2007046703, WO2007148971, WO2009014445, WO2009104964, WO03042361, WO2008024998, WO2010114948, which are incorporated herein by reference.

In another embodiment, a method is provided for determining human patients eligible for a medical treatment with an AAV5 gene therapy vector comprising the steps of:
  providing a serum sample from a human patient;
  determining the anti-AAV5 antibody titer;
  wherein patients can be considered eligible for a medical treatment if the total anti-AAV5 antibody titer has a value in the range of 0.02-5 as determined with a total anti-AAV5 antibody (TAb) assay as described in the examples.
  Optional, said method comprises subsequently the step of:
  administering to the eligible human patient an AAV5 gene therapy vector.

It is understood that any of the meets and bounds as described above with regard to embodiments related to the medical use of AAV5 gene therapy factors also apply to any of the methods as described herein, e.g. for methods of delivery of an AAV5 gene therapy vector or for determination of eligibility. Preferably, said total anti-AAV5 antibody titer has a value in the range of 0.02-4, 0.02-3, or 0.02-2 as determined with a total anti-AAV5 antibody (TAb) as described in the examples.

In another embodiment, a method for determining human patients eligible for a medical treatment with an AAV5 gene therapy vector comprises the steps of:
providing a serum sample from a human patient;
determining the anti-AAV5 antibody titer;
wherein patients can be considered eligible for a medical treatment if the neutralizing anti-AAV5 antibody titer has a value in the range of 3-10,000 as determined with a neutralising anti-AAV5 antibody (NAb) assay as described in the examples.
Optional, said method comprises subsequently the step of:
administering to an eligible human patient an AAV5 gene therapy vector.

Preferably, said anti-AAV5 antibody titer has a value in the range of 3-5,000, 3-3,000, or 3-1,000 as determined with a neutralising anti-AAV5 antibody (NAb) as described in the examples.

It is understood that the above described eligibility criterium is not the sole criterium that can be used for selecting an AAV5 gene therapy treatment. Hence, when the human patient complies with all other criteria, the anti-AAV5 antibody criterium determines eligibility of the human patient.

In another embodiment, a method of treating a human is provided comprising administering an effect amount of an AAV5 gene therapy vector to a human in need thereof;
wherein said human is not subjected to a pre-screening with an assay to determine anti-AAV5 antibodies;
and wherein said human has not been subjected to a medical treatment with an AAV5 gene therapy vector prior to said medical treatment.

In still a further embodiment, a method of treating a human is provided comprising administering an effect amount of an AAV5 gene therapy vector to a human in need thereof;
wherein said human is subjected to a pre-screening with an assay to determine anti-AAV5 antibodies;
wherein said human has not been subjected to a medical treatment with an AAV5 gene therapy vector prior to said medical treatment;
and wherein said human has an anti-AAV5 antibody level corresponding to at most the 95th percentile of anti-AAV5 antibody levels as observed in the human population.

In another further embodiment, a method is provided of delivering a gene to a human comprising administering an effective amount of an AAV5 gene therapy vector to a human in need thereof;
wherein said human is subjected to a pre-screening with an assay to determine anti-AAV5 antibodies;
wherein said human has not been subjected to a medical treatment with an AAV5 gene therapy vector prior to said medical treatment;
and wherein said human has an anti-AAV5 antibody level corresponding to at most the 95th percentile of anti-AAV5 antibody levels as observed in the human population.

In another embodiment, a method is provided of delivering a gene to a human comprising administering an effective amount of an AAV5 gene therapy vector to a human in need thereof;
wherein said human is not subjected to a pre-screening with an assay to determine anti-AAV5 antibodies;
wherein said human has not been subjected to a medical treatment with an AAV5 gene therapy vector prior to said medical treatment.

Alternatively, or in combination with any one of the preceding embodiments, in a preferred embodiment, the AAV5 vector composition further comprises a pharmaceutically acceptable carrier, diluents, solubilizer, filler, preservative and/or excipient. The rAAV vector bearing a therapeutic gene may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose. The viral vector is administered to a human patient in sufficient amounts as described above to transfect the desired cells and provide sufficient levels of transduction and expression of the selected transgene to provide a therapeutic benefit without undue adverse or with medically acceptable physiological effects which can be determined by those skilled in the medical arts.

Examples

Study Design and Participants

A multi-national, open-label, dose-escalation phase 1/2 study was carried out including adult males with severe (FIX<1 IU/dL) or moderate-severe (FIX≤2 IU/dL) haemophilia B who required either: 1) continuous FIX prophylaxis, or 2) on-demand FIX and have either ≥4 bleeds per year or haemophilic arthropathy. Further details of the trial may be found at the website of the NIH clinicaltrials.gov (NCT02396342). The study was approved by the Institutional Review Board/Institutional Ethics Committee at each centre. All participants provided written informed consent. The trial was performed according to the Declaration of Helsinki and the principles of Good Clinical Practice.

An AAV5 vector incorporating a codon-optimised wild-type hFIX gene under the control of a liver-specific promoter LP1 (Nathwani et al. N Engl J Med 2011; 365(25): 2357-65 and Nathwani et al. B. N Engl J Med 2014; 371(21): 1994-2004) was used in the study. The vector was manufactured using a baculovirus expression system in accordance with Good Manufacturing Practices. The vector genomic copy titers (gc) were determined using qPCR. The capsid to gc ratio was about 10, i.e. the amount of capsid was about ten-fold the amount of genomic copies. Capsid titer can be determined by High Performance Liquid Size Exclusion Chromatography (HPL-SEC) with UV absorption detection. The method is based on a SEC column, which is chosen for its capacity to separate AAV particles from smaller matrix components. In the method, a calibration curve is generated using an AAV vector preparation with known total particle concentration. In the calibration curve, amounts of injected total particles are plotted against response data. Using the returned AAV peak area and the calibration curve, the amount of injected sample particles is calculated by means of interpolation. The AAV5 vector was administered as a single, 30-minute, peripheral intravenous infusion. Participants were treated in two consecutive, escalating dose cohorts: Cohort 1 (n=5, participants 1-5) received $5 \times 10^{12}$ gc/kg and Cohort 2 (n=5, participants 6-10) $2 \times 10^{13}$ gc/kg. Cohort 1 consisted of adult males with an average age of 69 years (35-72) and an average body weight of 84.5 kg (71.2-89.1), cohort 2 consisted of adult males with an average age of 35 years (33-46) and an average body weight of 84.0 kg (71.4-96.0). Efficacy outcome measures included FIX plasma activity measurements. Furthermore, sera from the subjects were obtained for Neutralizing AAV5 antibody titer (NAb titer) and Total AAV5 antibody titer (TAb) analysis.

Control sera from healthy donors were commercially obtained from SeraLab (West Sussex, UK). All information provided pertaining to these sera is listed below

TABLE 1

Healthy donors. Control Sera

| LOT#: | GENDER: | AGE: | ETHN: |
|---|---|---|---|
| 1 | MALE | 33 | BLACK |
| 2 | MALE | 53 | BLACK |
| 3 | MALE | 41 | BLACK |
| 4 | MALE | 49 | HISPANIC |
| 5 | MALE | 59 | HISPANIC |
| 6 | MALE | 45 | HISPANIC |
| 7 | MALE | 41 | HISPANIC |
| 8 | MALE | 23 | HISPANIC |
| 9 | MALE | 39 | BLACK |
| 10 | MALE | 37 | BLACK |
| 11 | FEMALE | 38 | BLACK |
| 12 | FEMALE | 27 | HISPANIC |
| 13 | FEMALE | 48 | HISPANIC |
| 14 | FEMALE | 49 | CAUCASIAN |
| 15 | FEMALE | 31 | BLACK |
| 16 | FEMALE | 23 | HISPANIC |
| 17 | FEMALE | 45 | BLACK |
| 18 | FEMALE | 30 | HISPANIC |
| 19 | FEMALE | 36 | BLACK |
| 20 | FEMALE | 25 | HISPANIC |
| 21 | MALE | 59 | CAUCASIAN |
| 22 | MALE | 50 | CAUCASIAN |
| 23 | MALE | 54 | CAUCASIAN |
| 24 | MALE | 57 | CAUCASIAN |
| 25 | MALE | 65 | CAUCASIAN |
| 26 | MALE | 57 | CAUCASIAN |
| 27 | MALE | 59 | CAUCASIAN |
| 28 | MALE | 54 | CAUCASIAN |
| 29 | MALE | 48 | CAUCASIAN |
| 30 | MALE | 41 | CAUCASIAN |
| 31 | MALE | 52 | CAUCASIAN |
| 32 | MALE | 57 | CAUCASIAN |
| 33 | MALE | 52 | CAUCASIAN |
| 34 | MALE | 50 | CAUCASIAN |
| 35 | MALE | 51 | CAUCASIAN |
| 36 | FEMALE | 24 | CAUCASIAN |
| 37 | FEMALE | 28 | CAUCASIAN |
| 38 | FEMALE | 54 | CAUCASIAN |
| 39 | FEMALE | 23 | CAUCASIAN |
| 40 | FEMALE | 47 | CAUCASIAN |
| 41 | FEMALE | 27 | CAUCASIAN |
| 42 | FEMALE | 39 | CAUCASIAN |
| 43 | FEMALE | 35 | CAUCASIAN |
| 44 | FEMALE | 24 | CAUCASIAN |
| 45 | FEMALE | 47 | CAUCASIAN |
| 46 | FEMALE | 57 | CAUCASIAN |
| 47 | FEMALE | 55 | CAUCASIAN |
| 48 | FEMALE | 46 | CAUCASIAN |
| 49 | FEMALE | 21 | CAUCASIAN |
| 50 | FEMALE | 51 | CAUCASIAN |

Neutralizing AAV5 Antibody (NAbs) Titer

The measurement of NAbs in human serum was assessed based on a highly sensitive in vitro assay using AAV5 carrying the transgene luciferase (AAV5-luc) and the human embryonic kidney cell line HEK293T (ATCC 11.268). Transgene expression is revealed by addition of luciferin analog.

Materials Used:
HEK293T cells (HEK293T/ATCC 11.268)
DMEM with phenol red (Gibco, REF #31966)/10% FBS (Greiner, REF #758093)/1% PenStrep (Gibco, REF #15140)
DMEM without phenol red (Gibco, REF #21063)/1% Pen-Strep (Gibco, REF #15140)
1×PBS−/−(Gibco, REF #14190)
1× Trypsine EDTA (Gibco, REF #25200)
poly-L-lysine (PLL) solution (2.5%) (Sigma-Aldrich, REF #8920-100)
96-well flat bottom black culture plates (costar, REF #3916)
transparent 96-well flat bottom plates (corning, REF #3596)
ONE-Glo Luciferase Assay System (Promega, REF #E6120)
Glo Lysis Buffer, 1× (Promega, REF #E2661)
AAV5-CMV-luc (e.g. AAV5-CMV-73QlucHtt from PKO was used, titer: 4e13 gc/ml)

Basically, cells were seeded into a black 96-well plates and transparent 96-well plates by adding 100 µl/well of HEK293T cells in DMEM (with phenol red/10% FBS and 1% P/S (Penicillin/Streptomycin)) at a concentration of $0.5 \times 10^5$ cells/well. Cells were incubated overnight.

The next day, serial dilutions of plasma on transparent 96-well plates in medium (DMEM/1% PS without phenol red/10% FBS) were prepared. The final plasma dilutions, after addition of virus (see below), there were obtained were 2, 4, 8, 16, 32, 64, 128, 256, 512, and 1024.

Dilutions were prepared by adding 140 µl of medium to the wells designated A2-A11 (negative control wells), and 70 µl of medium is added to the rest of the rows in columns 3, 4, 5, 6, 7, 8, 9, 10 and 11 of the plate and to H2-H11 row (positive control). Plasma samples are added to the wells B2, C2, D2, E2, F2, G2 (140 µl/well) which resulted in the first dilution: 1. Consequently serial dilutions of plasma are performed across the plate by transferring 70 µl from column 2 to column 3 (dilution 2), from 3 to 4 (4), from 4 to 5 (8), from 5 to 6 (16), from 6 to 7 (32), from 7 to 8 (64), from 8 to 9 (128), from 9 to 10 (256), from 10 to 11 (512) then 70 µl from column 11 is discarded. AAV5-CMV-73QlucHtt is prepared in medium (DMEM/1% PS without phenol red/10% FBS) at $6 \times 10^9$ gc/ml. Next 70 µl/well of $6 \times 10^9$ gc/ml of AAV5(160)-CMV-73QlucHtt virus dilution is added to the plasma dilution plates, excluding wells A2-A11 (negative controls). The plates are carefully placed on a plate shaker for 2 min at 300 rpm. The plates are then incubated for 1 h at 4 degrees Celsius.

The culture medium is removed from black 96-well plates that were prepared on the previous days (with the HEK293T cells) and replaced the prepared plasma dilutions by pipetting from the transparent plates into black plates with Hek293T cells in a volume of 100 µl/well. These plates were incubated for 16-20 h at 37° C. The next day, the cells were equilibrated at room temperature and medium was removed. Cells were rinsed once with 1×PBS−/−(100 µl/well) after which 100 µl/well of Glo Lysis Buffer was added to the plates and incubate for 5 minutes at room temperature to allow lysis to occur. After this, 100 µl/well of reagent from ONE-Glo Luciferase Assay System is added (Reagent is prepared according to manufacturer's instructions). After at least 3 minutes, the plates are measured with the use of ONE-Glo Protocol on GloMax Discover machine. Anti-AAV5 neutralizing antibody titer is determined with the use of LabKey software analysis that calculates the percent of neutralization for each serum dilution after subtraction of background activity, and then fits a curve to the neutralization profile. It then uses this curve to calculate neutralizing antibody titers for chosen benchmark, area-under-the-curve (AUC), and error estimates. The four-parameter method was used to calculate curve fits. LabKey calculates IC50, the dilution at which the antibodies inhibit transduction by 50%. LabKey also calculates "point-based" titers according to Johnson and Byington, Techniques in HIV Research. New York, N.Y.: Stockton Press, 1990: 71-76. This is done by linearly interpolating between the two replicates on either side of the target neutralization percentage. Each run included positive controls (wells without sample sera but with AAV5-LUC), negative controls (wells that have only medium, without sample sera and without AAV5-LUC) and negative control sample serum (heat inactivated FBS) to assess the specificity of AAV5-LUC neutralization. FBS should not have anti-AAV5 neutralizing properties when measured as a sample.

Anti-AAV5 Antibody Titer

The quantification of total human Abs against AAV5 was based on an ELISA assay using the specific capsid to coat the plate. The presence of total human Abs specific against AAV5 capsid is revealed using Protein A Peroxidase. ELISA plates (Nunc MaxiSorp plate. Ref: 456537, Thermo Scientific) were coated with antigen (AAV5 cap) at 100 ng/well in carbonate buffer overnight to 4° C. The next day plates were washed three times with PBS tween-20 (PBSt) to eliminate the rest of the antigen and blocked with blocking solution (PBS+3% FBS) to prevent unspecific binding. After washing three times with 200 µL PBSt, human serum dilutions in PBSt were added, starting with 1:9 followed by a dilution series of 1:3 in a final volume of 100 µL. All samples were tested in duplicate. Negative controls without human serum were included in each plate. The serum dilutions were incubated for 2 h at 37°. After this, the serum was removed, the plate was washed three times with PBSt, and 100 µL of protein A peroxidase diluted 1:10,000 in blocking solution were added for one hour. The plate was washed three times with PBSt and the reaction was revealed with TMB substrate and stopped 30 min later with $H_2SO_4$ 2 N. The absorbance was read at 450 nm in a microplate reader. The total antibody titre was calculated as the serum dilution which had an absorbance five-fold higher than the negative control.

Results and Discussion

The human patients in both cohorts all presented meaningful improvements in FIX activity, with most human patients improving by a change in phenotype from severe to mild (table 2), resulting in a substantial reduction or even absence of use of prophylactic administration of FIX protein. There was variation observed between the FIX activity levels observed between patients and between cohorts. The variation in FIX activity levels did not correlate with the NAb or TAb status of the human patients.

Figure 1B:
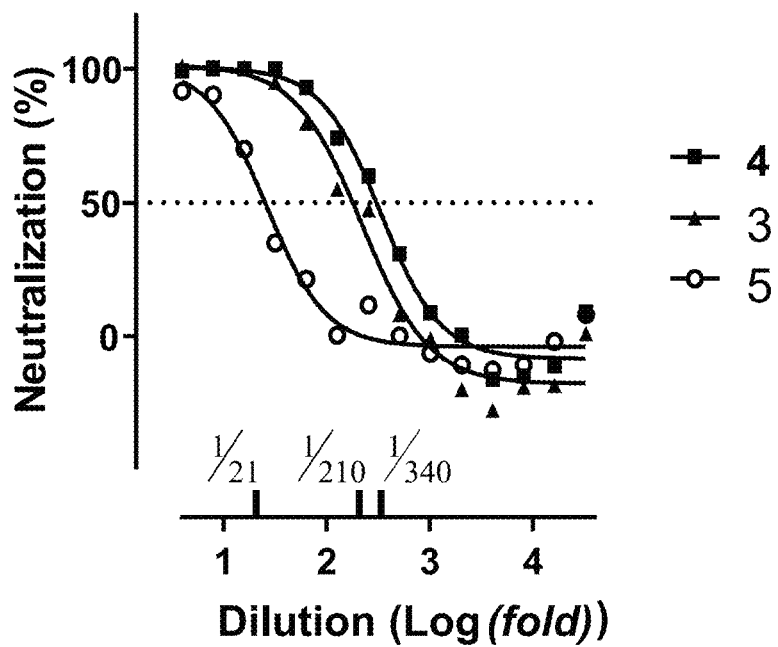
Figure 2A:
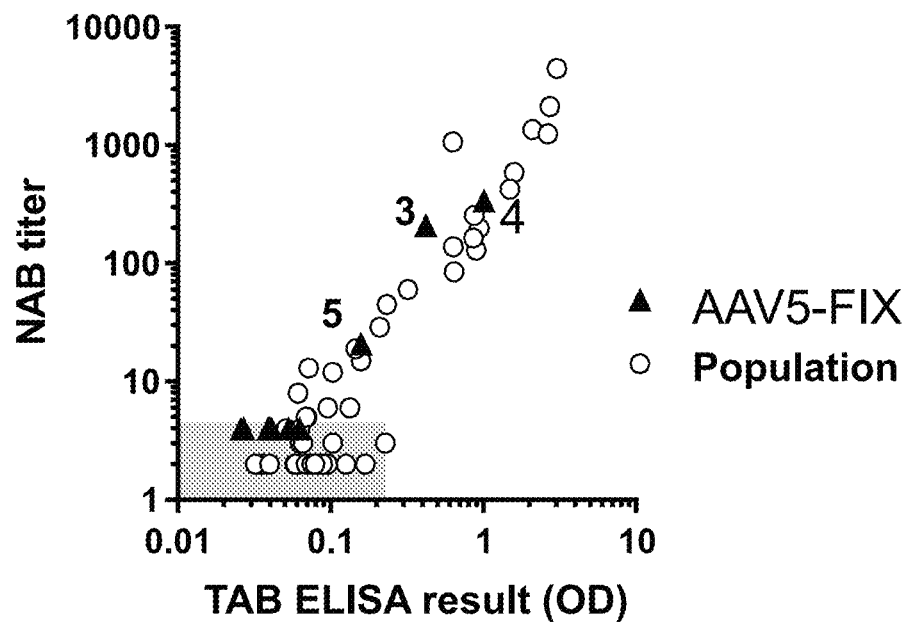
FIG. 2A: AAV5-neutralizing antibodies versus total anti-AAV5 antibodies. Neutralizing (NAb) titer versus total (TAb) ELISA results as reported in the population screening study. Each open symbol represents paired NAb and TAb results of one healthy individual. NAb and TAb results of treated patients are shown superimposed (▲, with study subjects 3, 4 and 5 as specified).
Figure 2B:
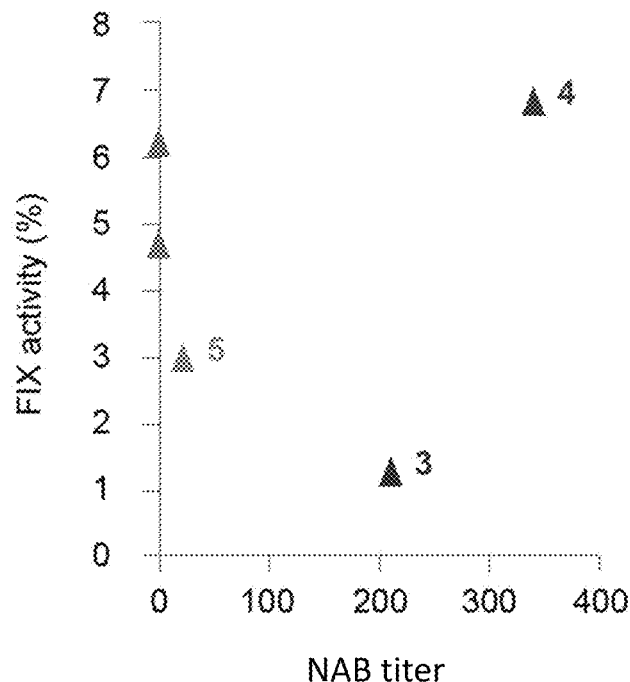
FIG. 2B: AAV5 NAb Titer versus FIX levels. The percentage of FIX activity in cohort 1 post-dosing is plotted against the NAb titer pre-dosing.

Previously reported prevalence of TAb against AAV5 (40%, Boutin et al. Hum Gene Ther. 2010 Jun. 21(6):704-712) roughly corresponded with the results of the current analysis (30%). The results obtained with the luciferase-based NAb assay (see FIGS. 1 and 2) suggest that the prevalence of AAV5 (neutralizing) antibodies is similar, as a positive signal was returned for 14 of the 50 screened control sera (28%) which is in line with recent studies (Li C et al. Gene Ther. 2012 March; 19(3):288-94). The results from the sera obtained from the human patients prior to the gene therapy treatment is in line therewith as well wherein 3 out of 10 sera found positive in both the NAb assay and the Tab assay (30%). Total antibodies as assessed by ELISA and neutralizing antibodies as assessed by luciferase-based assay closely correlate, suggesting that both assays detect the same entity (see FIG. 2A).

Furthermore, the presence of neutralizing antibody titers post-treatment was also tested and found to be in the range of about $10^6$ and above. Hence, the antibody titers that were found in untreated humans, endemically acquired, is well outside the range of titers observed in human patients that were subjected to an AAV5 based gene therapy. Furthermore, patients with pre-existing AAV5 NAb demonstrated a rapid increase in IgG upon administration of AAV-FIX characteristic of an immune boost, in contrast to patients without NAbs, who showed a rapid and transient increase in IgM followed by a rise in IgG typical of first exposure to an antigen. Furthermore, there was no evidence of ALT (Alanine Aminotransferase) elevation or capsid specific T-cell activation in treated patients with pre-existing NAb. Hence, administration of AAV5-based gene therapy in patients with endemically-acquired pre-existing NAbs was well tolerated without ALT elevation or T-cell activation.

To conclude, the presence of anti-AAV5 antibodies, detected in vitro either by the NAb assay or the TAB assay was not predictive nor indicative for impairing transduction in vivo. There was no evident correlation between presence of Nabs before therapy and FIX levels after therapy resulting from the AAV5 FIX gene transfer. Strikingly, the highest responder in cohort 1, receiving the lower dose of AAV5 vector, also had the highest level of NAb and TAb antibodies detected. The range of anti-AAV5 titers observed in the healthy population indicate that the levels of antibodies in the healthy population, which have not been subjected to an AAV5 gene therapy treatment, do not impair transduction with AAV5 in vivo. This is because the highest titer observed in the healthy population is close within range of to the highest titer observed in patient 5 of cohort 1. Hence, it is considered feasible that testing for the presence or absence of anti-AAV5 antibodies in an untreated population is not required prior to treatment with an AAV5 gene therapy vector.

TABLE 2

Mean steady state FIX levels and prophylaxis status by participant Only values at least 10 days after last FIX administration are included; [a]Prophylaxis status is as of last visit. CI, confidence interval; FIX, factor nine; IU, international units.

| | Pre-treatment | | | Post-treatment | | | |
| --- | --- | --- | --- | --- | --- | --- | --- |
| Participant | FIX activity IU/dL | Haemophilia B phenotype | FIX prophylaxis | Mean steady state FIX, IU/dL activity (95% CI) | FIX Prophylaxis[a] | Haemophilia B phenotype | Reduction of severity |
| 1 | <1 | Severe | Yes | 6.2 (5.8-6.6) | No | Mild | Yes |
| 2 | <1 | Severe | Yes | 4.7 (4.5-5.0) | No | Moderate | Yes |
| 3 | <1 | Severe | Yes | 1.3 (−0.7-3.2) | Yes | Moderate-severe | Yes |

TABLE 2-continued

Mean steady state FIX levels and prophylaxis status by participant Only values at least 10 days after last FIX administration are included; [a]Prophylaxis status is as of last visit.
CI, confidence interval; FIX, factor nine; IU, international units.

| | Pre-treatment | | | Post-treatment | | | |
|---|---|---|---|---|---|---|---|
| Participant | FIX activity IU/dL | Haemophilia B phenotype | FIX prophylaxis | Mean steady state FIX, IU/dL activity (95% CI) | FIX Prophylaxis[a] | Haemophilia B phenotype | Reduction of severity |
| 4 | 1.5 | Moderate-severe | Yes | 6.8 (6.3-7.3) | No | Mild | Yes |
| 5 | <1 | Severe | Yes | 3.0 (2.6-3.4) | No | Moderate | Yes |
| 6 | <1 | Severe | Yes | 12.7 (11.9-13.5) | No | Mild | Yes |
| 7 | <1 | Severe | Yes | 6.4 (6.0-6.7) | No | Mild | Yes |
| 8 | <1 | Severe | No[b] | 6.8 (5.8-7.7) | No | Mild | Yes |
| 9 | <1 | Severe | Yes | 3.1 (2.8-3.3) | No | Moderate | Yes |
| 10 | <1 | Severe | Yes | 5.8 (5.4-6.2) | No | Mild | Yes |

The invention claimed is:

1. A method of treating a human disease comprising administering an effective amount of an AAV5 gene therapy vector to a human in need thereof; wherein the human is not subjected to a pre-screening with an assay to determine anti-AAV5 antibodies; and wherein the human has not been subjected to a medical treatment with an AAV5 gene therapy vector prior to the medical treatment.

2. The method of treating a human disease in accordance with claim 1, wherein the AAV5 gene therapy vector is administered at a dosage of at least $10^{12}$ capsids/kg.

3. The method of treating a human disease in accordance with claim 1, wherein the AAV5 gene therapy vector is administered at a dosage of at least $10^{12}$ gc/kg of body weight.

4. The method of treating a human disease in accordance with claim 1, wherein the AAV5 gene therapy vector is administered to a human having Hemophilia A or Hemophilia B.

5. The method of treating a human disease in accordance with claim 1, wherein the AAV5 gene therapy vector is administered to a human having Hemophilia, wherein the AAV5 gene therapy vector encodes a FIX protein or variant thereof.

6. The method of treating a human disease in accordance with claim 1, wherein the method comprises administering the AAV5 gene therapy vector into the bloodstream.

7. The method of treating a human disease in accordance with claim 4, wherein the method comprises administering the AAV5 gene therapy vector into the bloodstream.

8. The method of treating a human disease in accordance with claim 5, wherein the method comprises administering the AAV5 gene therapy vector into the bloodstream.

9. The method of treating a human disease in accordance with claim 6, wherein the AAV5 gene therapy vector is delivered to the liver via the bloodstream.

10. The method of treating a human disease in accordance with claim 1, wherein the AAV5 gene therapy vector is produced in insect cells.

* * * * *